(12) United States Patent
Young et al.

(10) Patent No.: US 9,468,865 B1
(45) Date of Patent: Oct. 18, 2016

(54) TINCTURE PREPARATION METHOD AND USE

(71) Applicants: Mary Young, Holiday, FL (US); Jason Young, Holiday, FL (US)

(72) Inventors: Mary Young, Holiday, FL (US); Jason Young, Holiday, FL (US)

( * ) Notice: Subject to any disclaimer, the term of this patent is extended or adjusted under 35 U.S.C. 154(b) by 0 days.

(21) Appl. No.: 14/630,470

(22) Filed: Feb. 24, 2015

(51) Int. Cl.
*B01D 11/02* (2006.01)
*A61K 36/00* (2006.01)
*A23F 3/18* (2006.01)

(52) U.S. Cl.
CPC .......... *B01D 11/0207* (2013.01); *A23F 3/18* (2013.01); *A61K 36/00* (2013.01); *B01D 11/0223* (2013.01)

(58) Field of Classification Search
CPC . A23F 3/18; B01D 11/0207; B01D 11/0223; A61K 36/00
See application file for complete search history.

(56) References Cited

U.S. PATENT DOCUMENTS

| | | | | |
|---|---|---|---|---|
| 5,725,895 A * | 3/1998 | Fahey | ............. | A21D 2/36 426/425 |
| 6,414,036 B1 * | 7/2002 | Ninkov | ............. | A61K 31/05 514/731 |
| 6,488,039 B1 * | 12/2002 | Chong | ............. | G05D 7/0635 134/186 |
| 8,445,034 B1 * | 5/2013 | Coles, Jr. | ............. | A61K 31/05 424/725 |
| 2014/0121391 A1 * | 5/2014 | Murphy | ............. | B01D 11/02 554/8 |

FOREIGN PATENT DOCUMENTS

CN 203710379 * 7/2014

OTHER PUBLICATIONS

English Translation for CN 203710379 published Jul. 2014.*

* cited by examiner

*Primary Examiner* — Anthony Weier
(74) *Attorney, Agent, or Firm* — Gulf Coast Intellectual Property Group

(57) ABSTRACT

A tincture and oil preparation apparatus that facilitates an automated method of manufacturing an herbal oil or tincture. The tincture and oil preparation apparatus includes a first container and a second container wherein the second container is suspendedly mounted within the first container. The first container includes a heating element, a control panel and a display screen. The control panel provides the ability to input cooking parameters for manufacturing of tinctures or oils. The cooking parameters include agitator speed, time and temperature. A lid having an electric motor and an agitator integrated therewith is operable to seal the first container and the agitator extends downward into the second container. The agitator is operable in a first speed category and a second speed category. The second container further includes mounting tabs operable to provide the suspended mounting of the second container within the first container.

9 Claims, 4 Drawing Sheets

TINCTURE PREPARATION METHOD AND USE

FIELD OF THE INVENTION

The present invention relates generally to tincture apparatus, more specifically but not by way of limitation, a tincture and herbal oil preparation apparatus that is operable to automate the tincture manufacturing process wherein the apparatus includes a first and second container and a plurality of automation features that facilitates the method of use.

BACKGROUND

Tinctures and herbal oils have been utilized for centuries. As is known in the art, tinctures are liquid extracts manufactured from herbs and the liquid is typically ingested orally by a user. Tinctures are typically alcohol extractions but other substances can be utilized during the extraction process such as but not limited to vegetable glycerin. Those individuals who prefer natural medicines and therapies traditionally utilize tinctures because their oral ingestion promotes quick entry into the blood stream.

The general method of preparation of a conventional tincture is a manual and time-consuming process. Typically herbs are placed into a container and an extracting liquid of typically forty percent or greater ethanol content is added to the container. The container is typically left idle at room temperature for several weeks wherein during that time period the container is periodically shaken so as to maximize extraction.

One problem with conventional methods of tincture is the amount of manufacturing time. As noted herein, basic tincture preparation can extend over a couple of weeks. Additionally, during the tincture manufacturing process, the material must be agitated in order to promote an improved extraction. Utilizing basic implements does not promote a timely and efficient manufacture of herbal tinctures. Further, without the ability to control the temperature of the tincture vessel, conventional tincture manufacturing is not as effective.

Accordingly, there is a need for a tincture preparation apparatus that is operable to provide automation of the tincture preparation process wherein the apparatus automates steps such as but not limited to agitation and temperature control.

SUMMARY OF THE INVENTION

It is the object of the present invention to provide a tincture preparation apparatus that facilities an automated process of preparing herbal tinctures and the like.

Another object of the present invention is to provide a tincture preparation apparatus that includes a first outer container and further includes a second container disposed within the interior volume of the first outer container that is operable to receive herbs and extracting liquid.

A further object of the present invention is to provide a tincture preparation apparatus that automates the preparation of herbal tinctures that includes a lid releasably secured to the first outer container wherein the lid includes an electric motor and an agitator wherein the agitator extends downward into the interior volume of the second container when the lid is secured to the tincture preparation apparatus.

An additional object of the present invention is to provide an automated tincture preparation apparatus that further includes the necessary electronics and elements so as to provide temperature control of the interior volume of the second container.

Still another object of the present invention is to provide an automated tincture preparation apparatus operable to facilitate an improved method of preparing tincture that further includes an overflow sensor mounted to the lid thereof.

An alternative object of the present invention is to provide an automated tincture preparation apparatus that further includes a thermometer operable to measure the temperature of the mixture within the interior volume of the second container.

Yet a further object of the present invention is to provide an automated tincture preparation apparatus that is operable to provide automated agitation of the mixture disposed within the interior volume of the second container.

Another object of the present invention is to provide an apparatus operable to facilitate the automated preparation of an herbal tincture that includes a central processing unit and graphical interface that is operable to provide a means to control time, temperature and agitation schedule.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
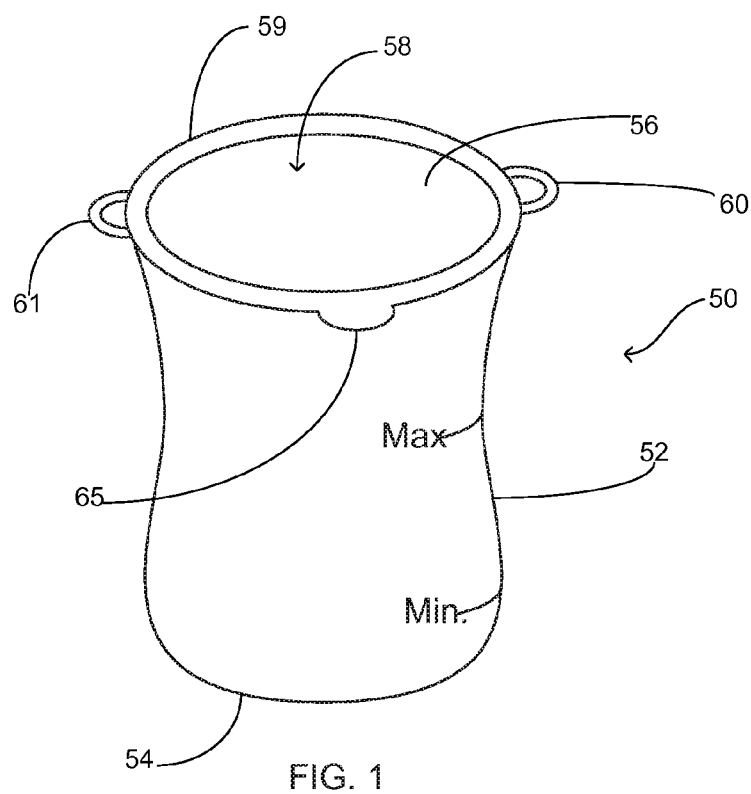
FIG. 1 is a perspective view of the internal container of the present invention.

Referring now to the drawings submitted herewith, wherein various elements depicted therein are not necessarily drawn to scale and wherein through the views and figures like elements are referenced with identical reference numerals, there is illustrated a tincture preparation apparatus 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Figure 3:
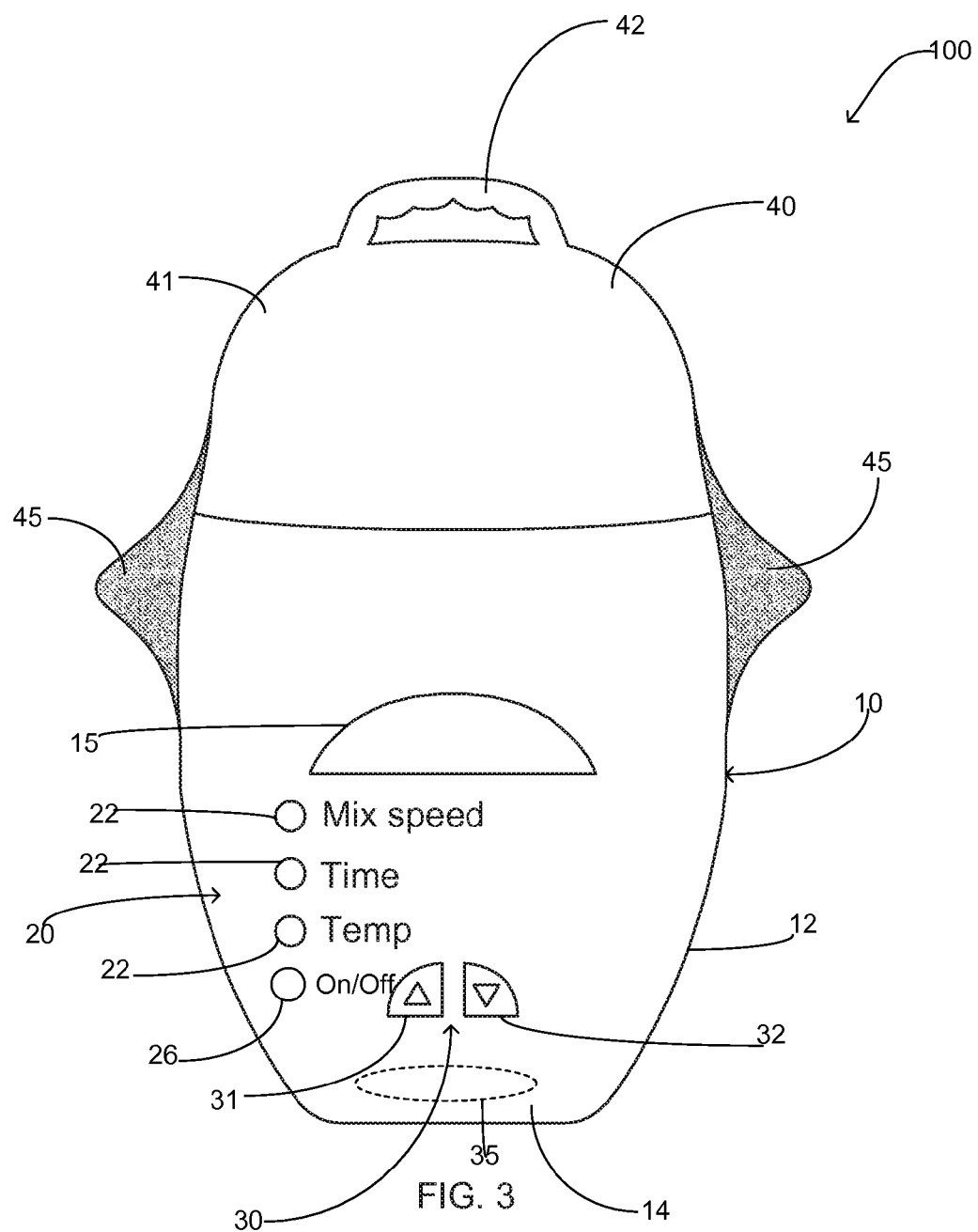
FIG. 3 is a front view of the present invention.

Referring in particular to FIG. 3 herein, the tincture preparation apparatus 100 further includes a first container 10 that is manufactured from a suitable material such as but not limited to metal. The first container 10 includes an outer wall 12 formed with a bottom 14 that are integrally formed to create an interior volume. While the first container 10 is illustrated herein as having a single wall forming a generally annular shaped container, it is contemplated within the scope of the present invention that the first container 10 could be formed utilizing more than one wall and further be provided in a plurality of different shapes. Integrally formed into the wall 12 of the first container 10 is a display screen 15. The display screen 15 is a conventional LCD or similar screen and functions to provide a user information such as but not limited to time and temperature data.

A control panel 20 is secured to wall 12 below the display screen 15 and functions to provide a user input interface. The control panel 20 consists of a plurality of selector switches 22 that facilitate the parameter selection to be controlled and set by a user. As is illustrated, it is contemplated within the scope of the present invention that the control panel 20 include the parameters of temperature, time and mixing speed. While these parameters are listed and illustrated herein, it is contemplated within the scope of the present invention that the control panel 15 could include additional selector switches 22 operable to provide user input for additional parameters. A control interface 30 is mounted to wall 12 and consists of a first button 31 and second button 32. The control interface 30 functions to adjust the selected parameter in either a positive or negative direction. By way of example but not limitation, a user would select the selector switch 22 for temperature and subsequently engage either first button 31 or second button 32 so as to adjust the temperature to the desired setting wherein the setting is displayed on the display screen 15. While not particularly illustrated herein, the tincture preparation apparatus 100 includes a conventional central processing unit that includes the necessary electronics to store, receive, transmit and manipulate data. The central processing unit is operably coupled to the control interface 30, control panel 20 and display screen 15. Further included in the first container 10 is a heating element 35. The heating element 35 is a conventional heating element and is integrally formed into the bottom 14 of the first container 10. The integral forming of the heating element 35 is desirable so as to inhibit any liquid coming in contact therewith.

The tincture preparation apparatus 100 further includes a lid 40 that is operable to cover the opening of the first container 10. The lid 40 includes an upper handle 42 that is formed proximate the top 41 and is operable to provide a user interface to engage the lid 40 during placing or removing the lid 40. The lid 40 is manufactured from a suitable durable material such as but not limited to metal and it is contemplated within the scope of the present invention that the lid 40 could be formed in various different shapes. Located on opposing sides of the tincture preparation apparatus 100 are locking handles 45. The locking handles 45 function to releasably secure the lid 40 to first container 10. The locking handles 45 utilize conventional fastening techniques and are manufactured from a heat resistant material such as but not limited to silicone rubber.

Referring in particular to FIG. 1, the second container 50 is illustrated therein. The second container 50 is manufactured from a durable thermally conductive material such as but not limited to metal. The second container 50 includes a wall 52 integrally formed with a bottom 54 forming interior volume 56 and opening 58. The second container 50 is manufactured in size so as to be insertable into the interior volume of the first container 10. While no illustrated herein, subsequent insertion of the second container 50 into the first container 10, a void exists therebetween. The void is important as it allows for more precise control of the internal temperature of the second container 50. As the heating element is activated during use of the tincture preparation apparatus 100 the void intermediate the first container 10 and second container 12 is heated and functions to provide a consistent thermal layer surrounding the second container 50. As relatively low temperatures are needed during the manufacture of tinctures, the void provides a technique to deliver a lower consistent temperature that surroundably encircles the second container 50. The second container 50 further includes mounting tabs 60, 61 formed with upper edge 59. The mounting tabs 60,61 are semi-circular in shape and are required to suspendedly mount the second container 50 within the first container 10 so as to create the aforementioned void. The mounting tabs 60,61 further function as a user interface for a user to place and/or remove the second container 50 within the interior volume of the first container 10. Further included proximate the upper edge 59 is a spout 65. Spout 65 is formed with upper edge 59 utilizing suitable techniques and is operable to provide assistance in the pouring of contents from the second container 50.

Figure 2:
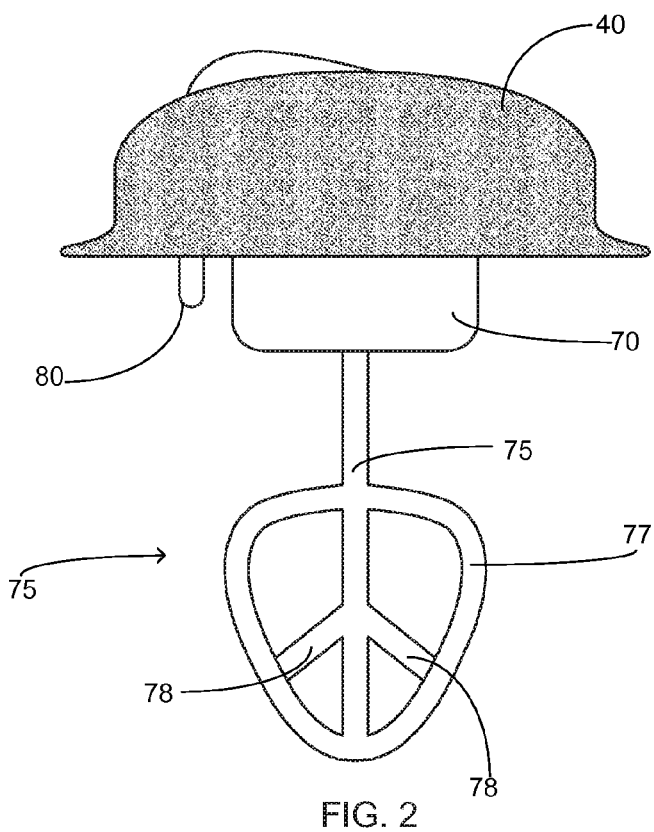
FIG. 2 is a side view of the top assembly of the present invention.

Referring in particular to FIG. 2 here, the lid 40 is illustrated therein. The lid 40 includes an electric motor 70 that is operable to drive an agitator 75. The electric motor 70 is a conventional electric motor and is operable coupled to the central processing unit of the tincture preparation apparatus 100. The agitator 75 extends downward from the lid 40 and includes blade 77 that is at least partially submersed into the contents placed within the interior volume 56 of the second container 50 ensuing lid 40 being placed on the first container 10. The agitator 75 is operational in varying different rotational speeds depending upon the mixing speed input by the user. The blade 77 includes mixing members 78 that are formed and spaced such that they do not damage any solid material placed within the interior volume 56 of the second container 50 but merely agitate so as to promote the extraction process facilitated by the method of the tincture preparation apparatus 100. Mounted to the lid 40 on the internal surface 39 thereof is an overflow sensor 80. The overflow sensor 80 is a transistor style switch that is operable to detect any liquid overflow that may occur from the second container 50. The overflow sensor 80 is coupled to the central processing unit and in the event of a liquid overflow will transmit a signal to the central processing unit so as to shut down the tincture preparation apparatus 100.

Figure 4:
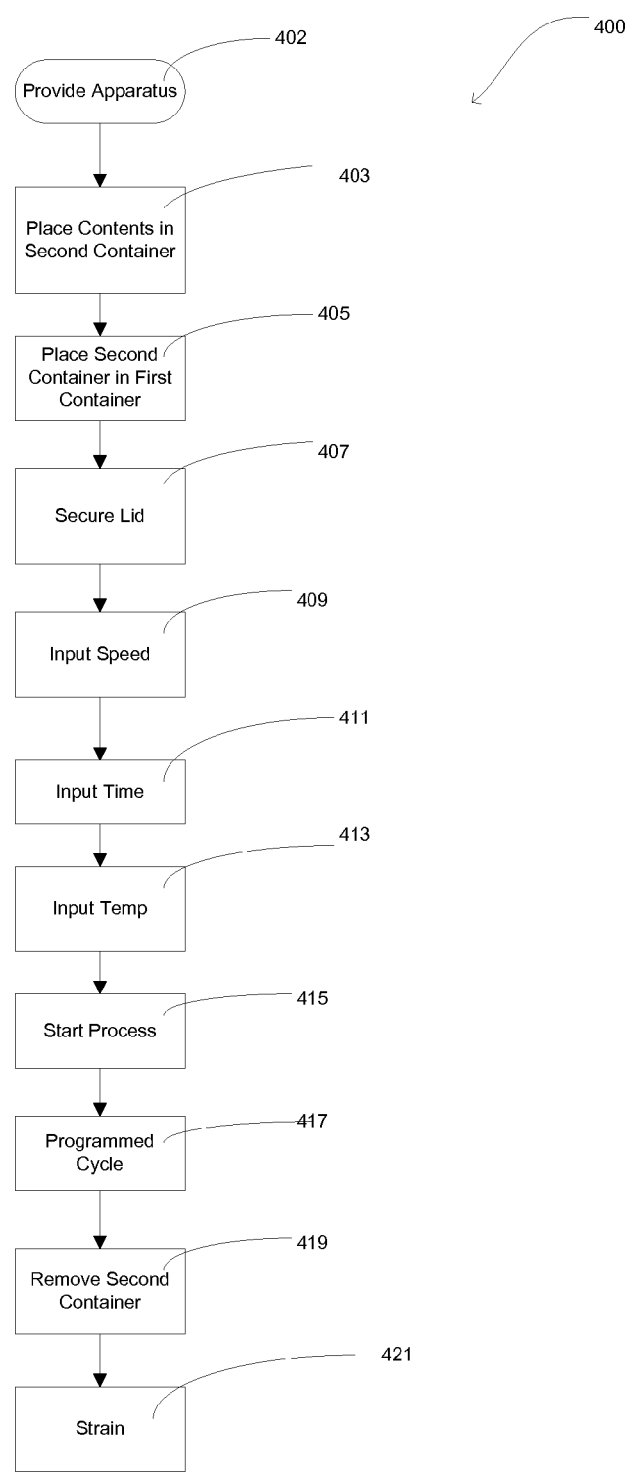
FIG. 4 is a flow chart of a preferred method of oil infusion and tincture preparation of the present invention.

Referring in particular to FIG. 4, a method of oil infusion and tincture preparation is outlined therein. In step 402, the tincture preparation apparatus 100 is provided to a user. Step 403 comprises of placing the desired contents within the interior volume 56 of the second container 50. In step 405, the user places the second container 50 into the first container 10. Step 407, the lid 40 is secured utilizing the locking handles 45. In step 409, the user will engage the control panel 20 so as to input the speed of the agitator 75. It is provided in the present invention that the user can enter speeds of the agitator 75 that are either a consistent rotation at various speeds or intermittent rotations. By way of example but not limitation, an intermittent rotation would be rotating for one minute every ten minutes. In step 411, the user will input the amount of time desired for execution of the method. While no particular time intervals are required, good results have been achieved by utilizing time increments that are provided in one-hour increments. One hour increments facilitate improved mixing of contents creating an improved final product. Step 413, the user will input the desired temperature of the tincture preparation apparatus 100. As oil preparation is improved at low temperatures, it is desired within the scope of the present invention that the temperature range of the tincture preparation apparatus 100 is 100 to 250 degrees Fahrenheit. In step 415, the user will start the process by engaging the on/off switch 26. Step 417, the tincture preparation apparatus 100 executes the programmed parameters of the method. In step 419, upon completion of the programmed method the user will remove the second container 50 from the first container 10. Step 421, the user will strain the contents within the second container 50 into a vessel for storage.

Figure 5:
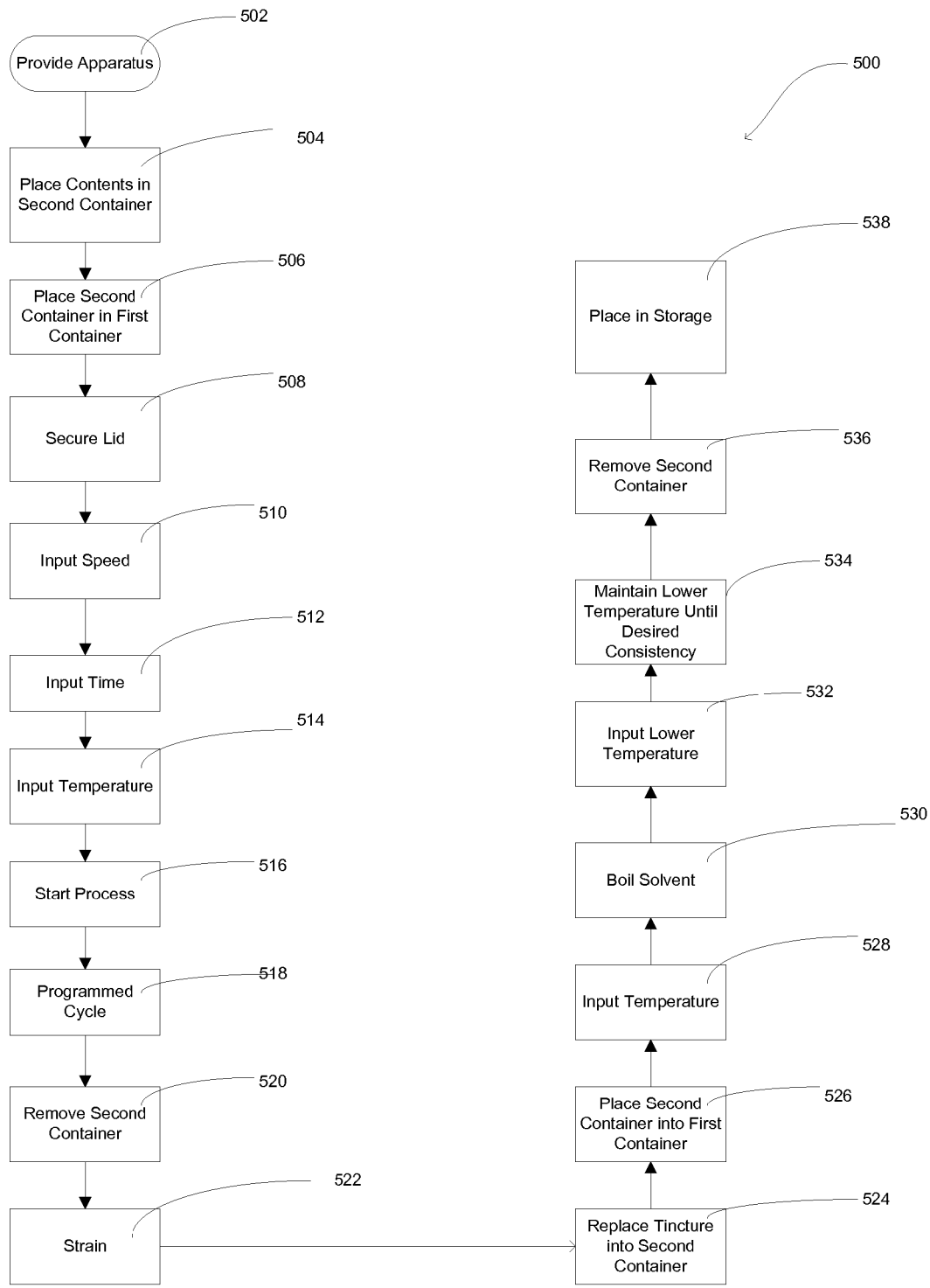
FIG. 5 is a flow chart of a preferred method of extracted oil preparation of the present invention.

Referring in particular to FIG. 5 herein, a preferred method of utilizing the tincture preparation apparatus 100 to prepare extracted oil preparation is as follows. In step 502, a user is provided with the tincture preparation apparatus 100. Step 504, a user will place an herb and a solvent within the interior volume 56 of the second container 50. In step 506, the user will place the second container 50 within the interior volume of the first container 10. Step 508, the user will secure the lid 40 utilizing the locking handles 45. In step 510, the user will engage the operating panel 20 and input the speed of the agitator 75. As previously discussed herein the agitator 75 speed can be consistent or intermittent rotations. The intermittent rotations are an important selection as it is desired during the tincture manufacturing process to agitate the contents within the second container 50 only occasionally. Step 512, the user will input the time period for the tincture preparation apparatus 100 to execute the method. In step 514, a temperature between the range of 100 to 250 degrees Fahrenheit is entered by the user. Step 516 the user will initiate the process by engaging the on/off switch 26. In step 518, the tincture preparation apparatus 100 will operate for the programmed cycle. Step 520, the user will remove the second container 50 from the first container 10. In step 522, the user will strain the tincture into an additional vessel. Step 524, the user will return the strained tincture into the interior volume 56 of the second container 50. In step 526, the user will replace the second container 50 into the first container 10. Step 528, the user will input a temperature that is sufficient to bring the solvent based tincture to a boil so as to boil off any remaining solvent. In step 530, the tincture preparation apparatus 100 will boil any solvent stored contained within the tincture mixture. Step 532, the user will reduce the temperature so as to be below the boiling point of the solvent forming a part of the tincture mixture. In step 534, the lower temperature is maintained until a desired consistency of the fully extracted oil is reached. Step 536, the second container 50 is removed from the first container 10. In step 538, the contents are poured from the second container 50 into a storage vessel.

While not particularly illustrated or discussed herein, it is noted that the tincture preparation apparatus 100 is powered by conventional AC power and would include the obvious elements of a power supply and an electrical cord.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A method for manufacturing a tincture or oil utilizing a tincture manufacturing apparatus comprising the steps of:
   providing a tincture manufacturing apparatus, said tincture manufacturing apparatus having a first container and a second container, said second container being insertable into said first container; said tincture manufacturing apparatus having a control panel on an outer wall of said first container, said control panel operable to facilitate the entry of a time parameter, a temperature parameter and a speed parameter, said tincture manufacturing apparatus further including a heating element, said heating element disposed in said first container, said tincture manufacturing apparatus further including a lid having an agitator extending downward therefrom;
   placing contents in said second container, wherein the contents are placed within an interior volume of said second container;
   inserting said second container into said first container, wherein the second container is suspendedly mounted within said first container;
   securing the lid onto the tincture manufacturing apparatus,
   inputting a speed parameter, wherein said inputting a speed parameter includes a first category and a second category, wherein said first category of the speed parameter is a consistent rotation of the agitator, wherein said second category of the speed parameter is an intermittent rotation of the agitator;

selecting a time parameter, said selecting a time parameter occurring in a discrete unit of time, wherein the discrete unit of time selected during selecting a time parameter are hour units;

inputting a temperature parameter, wherein the temperature parameter is within the range of 100 degrees to 250 degrees Fahrenheit;

initiating the cooking process, wherein in the cooking process the second container is heated to a temperature input from the step of inputting a temperature parameter, and wherein the agitator is rotated at a speed selected in said inputting a speed parameter;

monitoring for overflow, said monitoring for overflow being executed during the cooking process, said monitoring for overflow being accomplished by an overflow sensor, said overflow sensor being mounted on said lid;

completing the cooking process, wherein the tincture manufacturing apparatus completes the cooking process; and removing the second container from said first container, wherein the contents stored within the second container are strained into a storage vessel.

2. The method for manufacturing a tincture or oil as recited in claim 1, and further including the step of displaying parameters, said displaying parameters being provided on a display screen, said display screen being mounted to said first container.

3. The method for manufacturing a tincture or oil as recited in claim 2, and further including the step of providing mounting tabs, said mounting tabs being operably secured to said second container proximate an upper edge, said mounting tabs being located opposite each other on said upper edge, said mounting tabs operable to suspendedly mount said second container within said first container.

4. A method for manufacturing tincture or oil utilizing a tincture manufacturing apparatus wherein the method provides automation of the tincture manufacturing process comprising the steps of:

providing a tincture manufacturing apparatus, said tincture manufacturing apparatus having a first container and a second container, said first container having a wall and a bottom being integrally formed to form an interior volume, said first container having an opening opposite said bottom, said second container having a bottom and wall contiguously formed to create an interior volume, said second container having an opening opposite said bottom, said second container having an upper perimeter edge around said opening, said second container being insertable into said first container; said second container being suspendedly mounted within said first container, said tincture manufacturing apparatus having a control panel on an outer wall of said first container, said control panel operable to facilitate the entry of a time parameter, a temperature parameter and a speed parameter, said tincture manufacturing apparatus further including a heating element, said heating element disposed in said first container, said tincture manufacturing apparatus further including a lid having an agitator extending downward therefrom;

placing contents in said second container, wherein the contents are placed within an interior volume of said second container;

inserting said second container into said first container, wherein the second container is suspendedly mounted within said first container;

securing the lid onto the tincture manufacturing apparatus, inputting a speed parameter, wherein said inputting a speed parameter includes a first category and a second category;

selecting a time parameter, said selecting a time parameter occurring in a discrete unit of time;

inputting a temperature parameter, wherein the temperature parameter is within the range of 100 degrees to 250 degrees Fahrenheit;

initiating the cooking process, wherein in the cooking process the second container is heated to a temperature input from the step of inputting a temperature parameter, and wherein the agitator is rotated at a speed selected in said inputting a speed parameter;

completing the cooking process, wherein the tincture manufacturing apparatus completes the cooking process;

removing the second container from said first container;

straining the contents disposed within said second container into a vessel;

returning the tincture to the interior volume of the second container;

placing the second container into the interior volume of the first container;

inputting a temperature, wherein the inputting the temperature includes a temperature that is greater than that of a solvent that is disposed within said second container;

boiling the solvent;

inputting a second temperature, wherein the second temperature is lower than the boiling point of a solvent disposed within the second container, maintaining the second temperature, wherein the second temperature is maintained until contents disposed within the second container reaches a desired consistency;

removing the second container from the first container; and transferring the contents disposed within the second container into a storage vessel.

5. The method for manufacturing tincture as recited in claim 4, and further including the step of providing mounting tabs, said mounting tabs being operably secured to said second container proximate an upper edge, said mounting tabs being located opposite each other on said upper edge, said mounting tabs operable to suspendedly mount said second container within said first container.

6. The method for manufacturing tincture as recited in claim 5, and further including the step of monitoring for overflow, said monitoring for overflow being executed during the cooking process, said monitoring for overflow being accomplished by an overflow sensor, said overflow sensor being mounted on said lid.

7. The method for manufacturing tincture as recited in claim 6, wherein said first category of the speed parameter is a consistent rotation of the agitator.

8. The method for manufacturing tincture as recited in claim 7, wherein said second category of the speed parameter is an intermittent rotation of the agitator.

9. The method for manufacturing tincture as recited in claim 8, and further including the step of displaying parameters, said displaying parameters being provided on a display screen, said display screen being mounted to said first container.

* * * * *